United States Patent [19]

Yokoi et al.

[11] Patent Number: 4,734,169

[45] Date of Patent: Mar. 29, 1988

[54] PROCESS FOR PRODUCING HEXAFLUOROACETONE HYDRATE

[75] Inventors: Kazuma Yokoi; Takao Iida; Toshimasa Sagawa, all of Kitaibaraki, Japan

[73] Assignee: Nippon Mektron, Limited, Tokyo, Japan

[21] Appl. No.: 78,650

[22] Filed: Jul. 28, 1987

[30] Foreign Application Priority Data

Jul. 31, 1986 [JP] Japan ................................ 61-181098

[51] Int. Cl.$^4$ .............................................. C25B 3/02
[52] U.S. Cl. ........................................................ 204/79
[58] Field of Search ............................................ 204/79

[56] References Cited

U.S. PATENT DOCUMENTS 4,524,031  6/1985  Millaver et al. ...................... 204/79

Primary Examiner—R. L. Andrews
Attorney, Agent, or Firm—Fred Philpitt

[57] ABSTRACT

Hexafluoroacetone hydrate is obtained with a high current efficiency by electrolytically oxidizing dimer or monomer of hexafluoro-α-hydroxyisobutanoic acid in an electrolytic solution composed of an aqueous solution of (1) a nickel salt and (2) HCl, HBr or an alkali metal or alkaline earth metal thereof.

8 Claims, No Drawings

PROCESS FOR PRODUCING HEXAFLUOROACETONE HYDRATE

BACKGROUND OF THE INVENTION

1. Field of the Invention

This invention relates to a process for producing hexafluoroacetone hydrate, and more particularly to a process for producing hexafluoroacetone hydrate from hexafluoro-α-hydroxyisobutanoic acid.

2. Description of the Prior Art

Hexafluoroacetone is a monomer for producing a synthetic resin, a synthetic rubber, etc., or is used as an intermediate for cross-linking agents such as bisphenol AF, etc., or an intermediate raw material for medicaments, agricultural chemicals, etc.

The following processes have been so far proposed for producing hexafluoroacetone hydrate having the said applications.

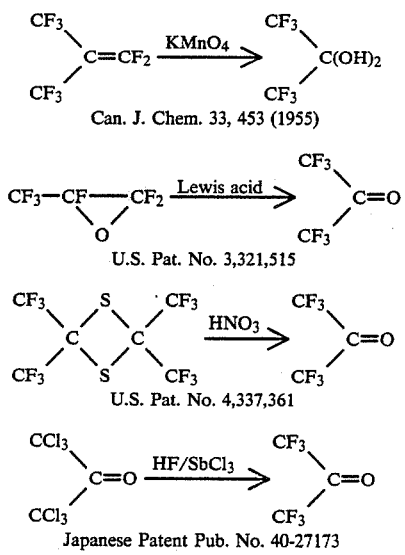

However, the foregoing processes have the following disadvantages.

(1) Oxidation reaction by potassium permanganate proceeds vigorously and the by-produced manganese dioxide is an industrial waste which is hard to treat.

(2) High purity oxide is hard to synthesize from hexafluoropropene and thus the produced hexafluoroacetone contains hexafluoropropene, etc.

(3) In the oxidation of hexafluorothioacetone dimer by nitric acid, the produced hexafluoroacetone hydrate contains $NO_2$ and $SO_2$, whose removed is troublesome.

(4) In the use of hexachloroacetone, chlorine not only contributes to increase the weight, but also is synthetically not efficient, and furthermore toxic antimony pentachloride is required. Thus, a high purity product is hard to obtain.

SUMMARY OF THE INVENTION

An object of the present invention is to provide a process for producing hexafluoroacetone hydrate from dimer or monomer of hexafluoro-α-hydroxyisobutanoic acid.

Another object of the present invention is to provide a process for producing hexafluoroacetone hydrate more advantageously than the conventional process based on oxidation by potassium permanganate, by-producing manganese dioxide or the process based on oxidation by expensive periodic acid.

Further object of the present invention is to effectively utilize octafluoroisobutene or its alcohol adduct.

DETAILED DESCRIPTION OF THE PREFFERED EMBODIMENT

The present inventors have found that the desired hexafluoroacetone hydrate can be obtained by once converting octafluoroisobutene or its alcohol adduct, whose effective utilization has been keenly desired, as a starting material to dimer or monomer of hexafluoro-α-hydroxyisobutanoic acid and then electrolytically oxidizing the dimer or monomer, on the basis of quite a different idea than these of the said prior art.

The thus obtained hexafluoroacetone hydrate can be used as such as a solvent for polyester, polyamide, etc., and its dehydration can be carried out according to a known process using phosphorus pentaoxide, concentrated sulfuric acid, sulfuric anhydride, or molecular sieve (Japanese Patent Application Kokai (Laid-open) Nos. 57-81,433 and 59-157,045). The present process also serves to produce hexafluoroacetone.

According to the present invention, hexafluoroacetone hydrate is produced by electrolytically oxidizing dimer of hexafluoro-α-hydroxyisobutanoic acid (1,1,1-trifluoro-2-trifluoromethyl-2-(3,3,3-trifluoro-2-trifluoromethyl-2acid)

$(CF_3)_2C(OH)COOC(CF_3)_2COOH$ or monomer thereof (3,3,3-trifluoro-2-hydroxy-2- trifluoromethyl-propionic acid)

$(CF_3)_2C(OH)COOH$ in an electrolytic solution comprising an aqueous solution of (1) a nickel salt and (2) hydrochloric acid, hydrobromic acid, or their alkali metal salt or alkaline earth metal salt.

Dimer of hexafluoro-α-hydroxyisobutanoic acid as a starting material is a novel substance and can be obtained by reacting hexafluoro-α-hydroxyisobutanoic acid ester with a hydroxide or a carbonate of an alkali metal or an alkaline earth metal. This reaction of the ester of hexafluoro-α-hydroxyisobutanoic acid and a hydrocarbon group such as alkyl, aryl or aralkyl is carried out in the presence of approximately a 0.5 to 5-fold amount of a solvent such as acetone, acetonitrile or tetrahydrofuran and an aqueous about 10 to about 50% solutoin of a metal hydroxide or carbonate catalyst by heating the rection mixture to a reflux temperature of the solvent for about 0.5 to about 3 hours, and then keeping the mixture at about 90° to about 100° C. for about 0.5 to about 5 hours while distilling off the solvent.

The metal hydroxide or carbonate as the catalyst includes, for example, sodium hydroxide, potassium hydroxide, potassium carbonate, calcium carbonate, etc., and is used in an about 1 to about 3 - fold molar amount on the basis of the isobutanoic acid ester. Furthermore an organic base such as triethylamine, pyridine, triethylenediamine (1,4-diazabicyclo(2,2,2)octane), 1,8-diazabicyclo(5,4,0)-7-undecene, 1,5-diazabicyclo(4,3,0)-non-5-ene, 4(dimethylamino)pyridine, etc. can be used together with the catalyst. After the completion of the reaction, hydrochloric acid, etc. are added to the reaction mixture to obtain the desired reaction product in the form of a free carboxylic acid.

Monomer of hexafluoro-α-hydroxyisobutanoic acid as the starting material can also be synthesized by oxidizing an alcohol adduct of octafluoroisobutene with an alkaline hydrogen peroxide, followed by hydrolysis in a solvent, as will be described below.

Octafluoroisobutene is a by-product obtained when hexafluoropropene, one of important starting materials for fluorine-containing copolymers, is produced, and this highly toxic octafluoroisobutene has a property of readily forming an alcohol aduct with a lower alcohol, for example, methanol, ethanol, n-propanol, isopropanol, n-butanol, etc.

Octafluoroisobutylalkyl ether as the alcohol adduct gives hexafluoro-α-hydroxyisobutanoic acid ester, when oxidized with an aqueous solution of potassium permanganate, and further gives hexafluoro-α-hydroxyisobutanoic acid, when hydrolyzed (Izv. Akad. Nauk SSSR Ser. Khim, February issue, 387–392 (1974)).

These dimer and monomer of hexafluoro-α-hydroxyisobutanoic acid can be used as a starting material for the present process, but the dimer is preferable from the viewpoint of easy separation and purification. In the case of the monomer, the monomer is usually produced as a solution in the acetone solvent as used in the reaction, and it is difficult to remove the acetone solvent from the solution. Furthermore, the monomer is highly water-soluble, and its isolation and preservation are troublesome. On the other hand, the dimer is readily separable from the reaction mixture only by acidifying the reaction mixture, and thus has such an advantage as easy post-treatment.

The electrolytic oxidation of the dimer and the monomer according to the present process seems to have the same reaction mechanism, and thus the reaction conditions are common to the dimer and the monomer. That is, it is possible to use a mixture of the dimer and the monomer.

In the case of monomer:

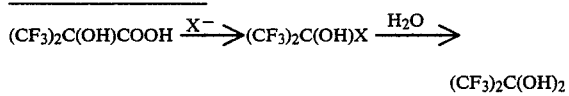

In the case of dimer:

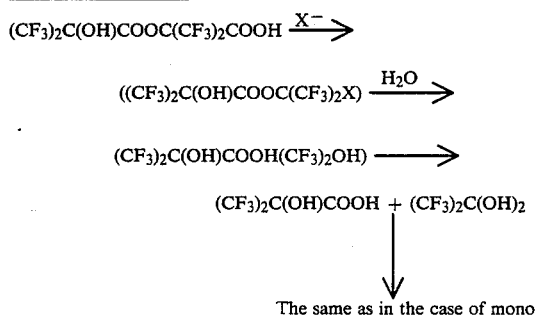

Electrolytic oxidation of the dimer or monomer of hexafluoro-α-hydroxyisobutanoic acid is carried out in the following conditions, using an aqueous solution of (1) a nickel salt and (2) hydrochloric acid, hydrobromic acid or a metal salt thereof. (1) As the nickel salt, nickel chloride is preferable. Beside the nickel chloride, nickel sulfate, nickel acetate, etc. which can form nickel chloride in an aqueous solution of hydrochloric acid can be used. The nickel salt is used in an amount of about 0.1 to about 20 g per l of the electrolytic solution. Without the nickel salt, the current efficiency is considerably lowered, or the reaction may fail to proceed at all.

Among hydrochloric acid, hydrobromic acid and then metal salts, hydrochloric acid and hydrobromic acid are preferably used. When these acids are used in such an amount as to make the pH of the electrolytic solution lower than 1, the reaction can proceed without any decrease in the current efficiency. When a metal salt, specifically an alkali metal salt represented by potassium chloride or an alkaline earth metal salt represented by barium chloride, is used, pH increases with the progress of electrolytic oxidation, and the electric current gradually fails to pass, thereby lowering the current efficiency. (2) Such an electrolytic solution as above, which further contains about 0.1 to about 30% by weight, preferably about 1 to about 20% by weight, of the dimer or monomer of hexafluoro- α-hydroxyisobutanoic acid is used for the electrolytic oxidation. (3) Electrolytic oxidation is carried out at an electrolysis voltage of 2.0 to 3.0 V, preferably 2.5 to 2.8 V, and a current density of 2.0 to 4.0 A/dm$^2$, preferably 2.4 to 3.0 A/dm$^2$. Outside the said electrolysis voltage range, the current efficiency will be lowered.

(4) Electrolysis temperature is about 10 to about 90° C., preferably about 50° to 70° C., more preferably about 60° C.

(5) As an anode, an isotropic carbon electrode fired at a firing temperature of about 1,000° C. is preferably used. The carbon electrode is used as such or pretreated in an electrolytic solution to be used or in an aqueous 10% nickel chloride solution. Besides the carbon electrode, platinum electrode, etc. can be used. As a cathode, electrodes of copper, iron, nickel, platinum, etc. are usually used. The interelectrode distance is usually set to about 0.1 to about 10 mm, preferably about 3 to about 6 mm.

After the electrolytic oxidation under these conditions, the reaction product hexafluoroacetone hydrate is extracted from the electrolytic solution by a water-insoluble, etheral solvent such as diethyl ether, diisopropyl ether, etc., and recovered as the desired product by distilling off the extracting solvent.

Hexafluoroacetone hydrate can be obtained according to quite a novel process based on electrolytic oxidation of the dimer or monomer of hexafluoro-α-hydroxyisobutanoic acid, which is more advantageous than the process based on oxidation by potassium permanganate by-producing manganese dioxide or the process based on oxidation by expensive periodic acid. In the case of hydrochloric acid or hydrobromic acid, the current efficiency will be as high as about 70 - about 80%.

The present invention will be described in detail below, referring to Examples, where the current efficiency and the conversion are calculated according to the following formulae:

Current efficiency =

$$\frac{\text{Quantity of electricity used for the production of the desired product } (F)}{\text{Total quantity of electricity used } (F)} \times 100(\%)$$

$$\text{Conversion} = \frac{\text{Desired product (in moles)}}{\text{Starting material (in moles)} + \text{Desired product (in moles)}} \times 100(\%)$$

REFERENCE EXAMPLE 1

126 g (0.558 moles) of methyl hexafluoro-α-hydroxyisobutanoate was dissolved in 360 ml of acetone, and admixed with 100 g of an aqueous 50% potassium hydroxide solution (0.893 moles in terms of KOH), whereby the temperature was elevated to about 40 to about 60° C. The mixture was heated under reflux for 3 hours, and then subjected to reaction at 90° C. for 2 hours, while distilling off acetone.

After the completion of the reaction, the reaction mixture was admixed with 50 ml of 35% hydrochloric acid, and the precipitates were recovered by filtration. To remove potassium chloride from the precipitates, the precipitates were dissolved in ethanol and the resulting solution was filtered and then distilled off ethanol, whereby 72 g of 2substituted hexafluoroisobutanoic acid represented by the following formula:

$$(CF_3)_2C(OH)COOC(CF_3)_2COOH$$

was obtained (decomposition point: 181°–183° C.; yield: 63.6%)

Elemental analysis (as $C_8H_2O_5F_{12}$):
Calculated: C: 23.66%, H: 0.50%, F: 56.14%.
Found C: 23.87%, H: 0.59%, F: 55.82%.
Infrared absorption spectra:

| Infrared absorption spectra: | |
|---|---|
| OH | 3380 cm$^{-1}$ |
| C=O | 1760 cm$^{-1}$ |
| C—O | 985 cm$^{-1}$ |
| $^{19}$F —NMR ($CF_3$ COOH basis): | |
| $CF_3$ | −0.4 ppm |

REFERENCE EXAMPLE 2

When 125 g of an aqueous 50% potassium carbonate solution (0.452 moles in terms of $K_2CO_3$) was used in place of the aqueous 50% potassium hydroxide solution in Reference Example 1, 59 g of 2-substitued hexafluoroisobutanoic acid was obtained (yield: 52.1%).

EXAMPLE 1

180 g of 2-substituted hexafluoroisobutanoic acid as obained in reference Examples was dissolved in an electrolytic solution prepared from 58 g of potassium chloride, 6 g of nickel chloride hexahydrate and 950 g of water, and an isotropic carbon anode and a copper cathode each having an available electrode surface of 144 cm$^2$ were dipped into the thus formed electrolytic solution and fixed therein at an interelectrode distance of 5 mm.

The solution temperature was elevated up to 60° C. while stirring the solution, and a voltage of 2.70 V was applied between the two electrodes. Electrolysis was carried out for 14 hours 20 minutes in such a state that an average current of 3.50A was passed through the solution, and then the solution was cooled. The reaction solution was quantitatively determined with $^{19}$F-NMR, using bisphenol AF as an internal standard substance, and it was found that the reaction proceeded well in the initial period of reaction with a current efficiency of 70%, whereas the current efficiency was reduced to less than 10% in the latter period of reaction and the reaction hardly proceeded, where the pH of the elecrolytic solution was about 4 and the conversion was 60%.

The reaction product was isolated from the reaction solution by extracting it into diisopropyl ether and then distilling off the extracting solvent, whereby 89 g of the desired hexafluoroacetone hydrate was obtained (yield: 55%).

EXAMPLE 2

In Example 1, 35.0 g of 36% concentrated hydrochloric acid was used in place of potassium chloride and the time of electrolysis was changed to 13 hours with an average current of 3.65 A. The current efficiency in the latter period of reaction was maintained at 60%. The current efficiency throughout the reaction was 78% and the conversion was 78%.

As a result of the reaction, 149 g of hexafluoroacetone hydrate was obtained (yield: 91%).

EXAMPLE 3

In Example 1, 92.5 g of potassium bromide was used in place of potassium chloride, and the time of electrolysis was changed to 15 hours with an average current of 4.01 A. The current efficiency was lowered in the latter period of reaction likewise as in Example 1. The current efficiency throughout the reaction was 45% and the conversion was 57%.

As a result of the reaction, 62 g of hexafluoroacetone hydrate was obtained (yield: 38%).

EXAMPLE 4

In Example 2, 59.4 g of 47% hydrobromic acid was used in place of 36% concentrated hydrochloric acid. The current efficiency throughout the reaction with an average current of 4.24 A was 70% and the conversion was 75%.

As a result of the reaction, 130 g of hexafluoroacetone hydrate was obtained (yield: 79%).

COMPARATIVE EXAMPLE 1

In Example 1, electrolysis was carried out for one hour without nickel chloride hexahydrate. No hexafluoroacetone hydrate was formed at all.

COMPARATIVE EXAMPLE 2

In Example 1, electrolysis was carried out for one hour without potassium chloride. No hexafluoroacetone hydrate was formed at all.

EXAMPLE 5

In Example 2, 190 g (0.896 moles) of hexafluoro-α-hydroxyisobutanoic acid obtained by hydrolysis of methyl hexafluoro-α-hydroxyisobutanoate was used in place of 2substituted hexafluoroisobutanoic acid, and the time of electrolysis was changed to 14 hours with an average current of 3.43 A. The current efficiency throughout the reaction was 73% and the conversion was 73%.

As a result of the reaction, 134 g of hexafluoroacetone hydrate was obtained (yield: 93%).

EXAMPLE 6

In Example 2, electrolysis was carried out by replacing 60 g out of 180 g of 2-substituted hexafluoroisobutanoic acid with hexafluoroisobutanoic acid. The current efficiency throughout the reaction with an average current of 3.60 A was 76% and the conversion was 76%.

As a result of the reaction, 152 g of hexafloroacetone hydrate was obtained (yield: 95%).

What is claimed is:

1. A process for producing hexafluoroacetone hydrate, which comprises electrolytically oxidizing 2-substituted hexafluoroisobutanoic acid represented by the following formula:

$$(CF_3)_2C(OH)COOC(CF_3)_2COOH$$

in an electrolytic solution composed of an aqueous solution of (1) a nickel salt and (2) hydrochloric acid, hydrobromic acid or an alkali metal salt or an alkaline earth metal salt thereof.

2. A process according to claim 1, wherein the electrolytic oxidation is carried out in the electrolytic solution containing the 2-substituted hexafluoroisobutanoic acid at a concentration of about 0.1 to about 30% by weight.

3. A process according to claim 1, wherein the electrolytic oxidation is carried out at an electrolysis voltage of 2.0 to 3.0 V and a current density of 2.0 to 4.0 A/dm$^2$.

4. A process according to claim 1, wherein the nickel salt in nickel chloride.

5. A process for producing hexafluoroacetone hydrate, which comprises electrolytically oxidizing hexafluoro-α-hydroxyisobutanoic acid represented by the following formula:

$$(CF_3)_2C(OH)COOH$$

in an electrolytic solution composed of an aqueous solution of (1) a nickel salt and (2) hydrochloric acid, hydrobromic acid or an alkali metal salt or an alkaline earth metal salt thereof.

6. A process according to claim 5, wherein the electrolytic oxidation is carried out in the electrolytic solution containing the hexafluoro-α-hydroxyisobutanoic acid at a concentration of about 0.1 to about 30% by weight.

7. A process according to claim 5, wherein the electrolytic oxidation is caried out at an electrolysis voltage of 2.0 to 3.0 V and a current density of 2.0 to 4.0 A/dm$^2$ 8. A process according to claim 5, wherein the nickel salt is nickel chloride.

* * * * *